United States Patent [19]

Seebach et al.

[11] Patent Number: 4,738,263
[45] Date of Patent: Apr. 19, 1988

[54] ELECTROSURGICAL ELECTRODE CONNECTOR

[75] Inventors: Timothy B. Seebach, Vandalia; James R. Crawford, Kettering, both of Ohio

[73] Assignee: Baxter Travenol Laboratories, Inc., Dayton, Ohio

[21] Appl. No.: 852,553

[22] Filed: Apr. 16, 1986

[51] Int. Cl.$^4$ ............ A61B 5/04; A61N 1/00
[52] U.S. Cl. ............ 128/640; 128/641; 128/639; 128/798
[58] Field of Search ........ 339/176 MF, 61 R, 75 R, 339/91 R, 36, 39, 67, 230 C, 234, 253; 128/641, 640, 303.17, 303.14, 303.13, 798, 639

[56] References Cited

U.S. PATENT DOCUMENTS

| | | | |
|---|---|---|---|
| 3,699,968 | 10/1972 | Bolduc | 128/313.03 |
| 3,842,394 | 10/1974 | Bolduc | 128/639 |
| 3,879,099 | 4/1975 | Shaffer | 439/397 |
| 3,895,635 | 7/1975 | Justus et al. | 128/303.13 |
| 4,014,343 | 3/1977 | Esty | 128/303.17 |
| 4,032,738 | 6/1977 | Esty et al. | 128/303.13 |
| 4,066,078 | 1/1978 | Berg | 128/641 |
| 4,094,571 | 6/1978 | Benjamin | 128/641 |
| 4,112,941 | 9/1978 | Larimore | 128/641 |
| 4,165,141 | 8/1979 | Williams et al. | 128/639 |
| 4,166,465 | 9/1979 | Esty et al. | 128/303.13 |
| 4,206,960 | 6/1980 | Tantillo | 128/303.13 |
| 4,273,135 | 6/1981 | Larimore et al. | 128/640 |
| 4,311,145 | 1/1982 | Esty et al. | 128/303.17 |
| 4,352,359 | 10/1982 | Larimore et al. | 128/640 |
| 4,550,961 | 10/1985 | Aicher | 439/348 |

Primary Examiner—William E. Kamm
Assistant Examiner—George Manuel
Attorney, Agent, or Firm—Killworth, Gottman, Hagan & Schaeff

[57] ABSTRACT

An electrical connector for providing electrical connection between a pair of electrical conductor leads, each having a ring terminal, and an electrically conductive connection tab of a medical electrode, including a pair of engagement holes, includes upper and lower connector portions which are permanently secured together, as by sonic welding, to hold the ring terminals in contact with the connection tab. The ring terminals are secured on posts where extend from one of the connector portions through engagement holes in the tab. Ribs on the posts hold the ring terminals in position during assembly of the connector. The connector includes outwardly curved surfaces adjacent an access opening for the conductor leads so as to transmit a portion of a force, which may be applied to the leads, to the connector and to relieve the terminals of a portion of such force.

14 Claims, 4 Drawing Sheets

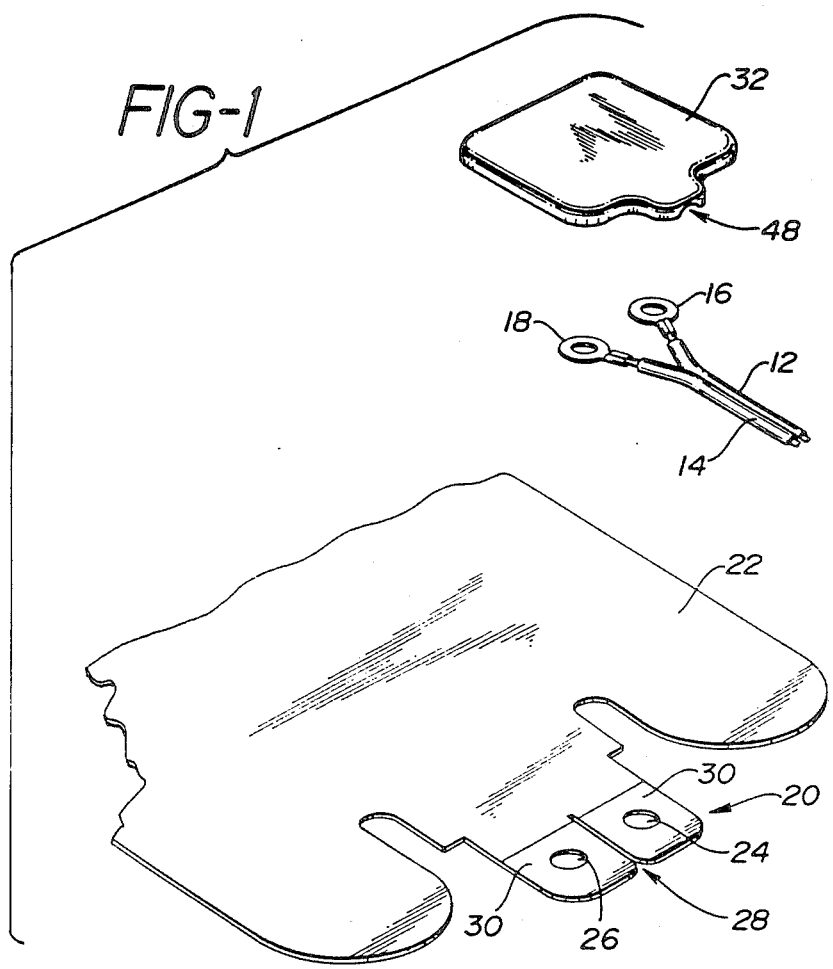
FIG-1
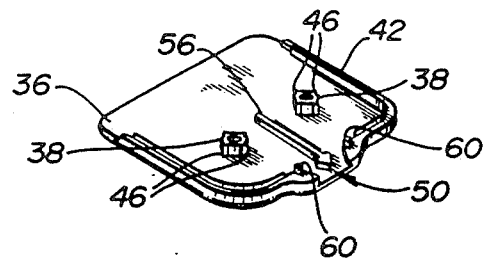

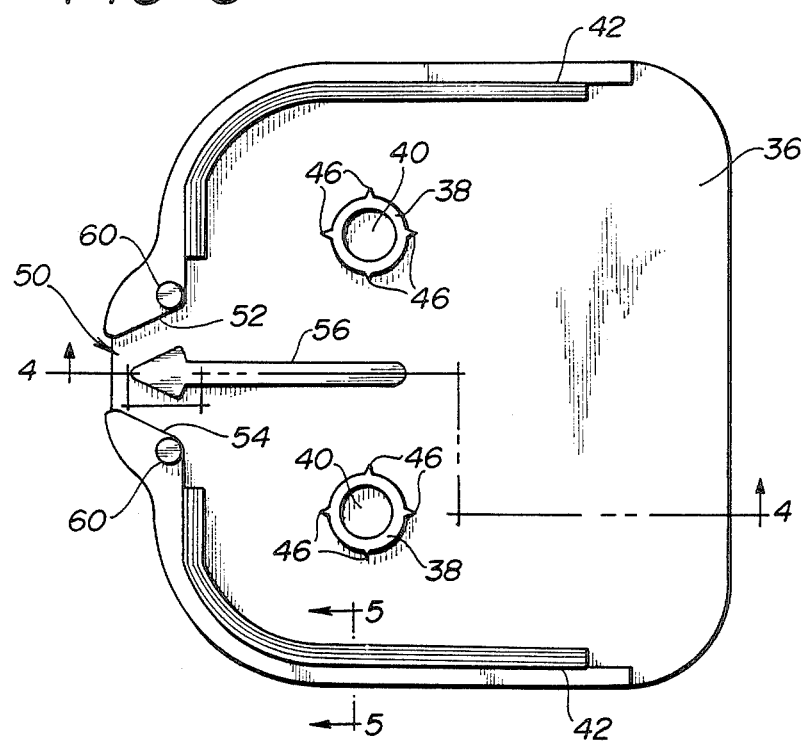

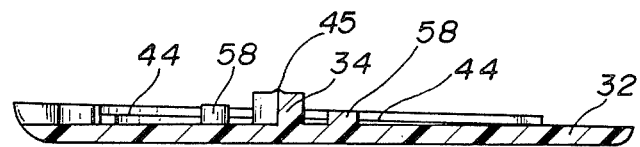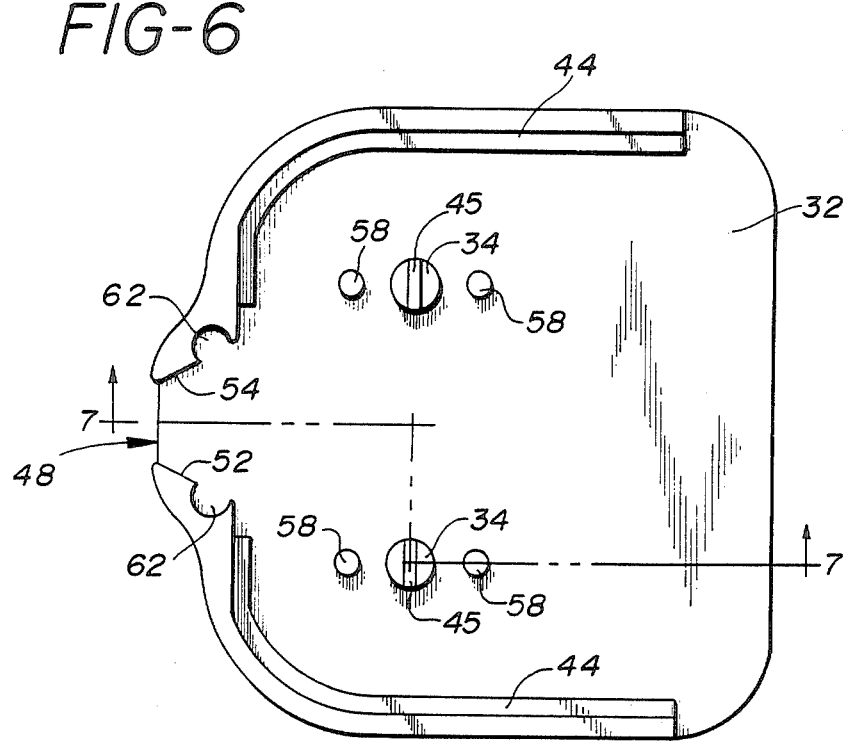

ELECTROSURGICAL ELECTRODE CONNECTOR

BACKGROUND OF THE INVENTION

The present invention relates to an electrical connector and, more particularly, to a connector specifically configured for permanent attachment to a medical electrode, such as an electrosurgical ground electrode.

In electrosurgical procedures, an electrical generator produces a high frequency electrical current which is applied to an active electrode. The active electrode may be configured as a scalpel which is used to cut tissue. The electric current causes coagulation at the incision, reducing bleeding. An indifferent or ground electrode, typically a single-use, disposable item, is attached to the patient and provides a return path to the generator for the high frequency current. The current supplied to the active electrode is concentrated in a relatively small area and high current densities are therefore obtained at the surgical site. It is essential, however, that the indifferent electrode provide for the current return to the generator over a relatively large surface area to maintain a low current density and thereby avoid injury to the tissue of the patient in this area.

It will be appreciated that it is of great importance that the current return path through the ground electrode to the electrosurgical generator remain unimpaired. If this current path should be interrupted, the electrosurgical current will be diverted to such alternate ground paths as may be available, such as for example, EKG electrodes attached to the patient or other grounded equipment in the operating room which may come into contact with the patient. Due to the much smaller surface area typically presented by such alternate ground paths, it is possible that the patient will be burned at the point where the current exits the patient's body.

It will be appreciated that not only must the ground electrode remain securely attached to the patient during the surgical procedure, but also the lead or leads from the electrosurgical generator must be securely connected to the ground electrode by an appropriate connector. In some cases, prior art disposable electrodes have been provided with a connection stud or tab to which a connector of a reusable lead assembly is attached. Connector arrangements for reusable lead assemblies are shown, for example, in U.S. Pat. Nos. 3,699,968, issued Oct. 24, 1972, to Bolduc; 3,842,394, issued Oct. 15, 1974, to Bolduc; 4,166,465, issued Sept. 4, 1979, to Esty et al; and 4,550,961, issued Nov. 5, 1985, to Aicher et al. Such a reusable lead assembly is economical since its cost is spread over many surgical procedures. Leads may, however, gradually deteriorate over time as a result of repeated folding and bending. If a lead assembly is not carefully checked on a routine periodic basis, the danger exists that a damaged lead might go unnoticed. Additionally, since the connector for such a lead assembly is specifically designed to be connected to and removed from numerous electrodes, the possibility of accidental disconnection of the connector from the electrode exists.

Other types of disposable ground electrodes have, in the past, been provided with a lead assembly which is permanently attached to the electrode, and discarded with the electrode after the completion of the surgical procedure. Such electrodes, although more expensive, are advantageous in that no periodic inspection and maintenance program is required for the electrode leads, since a new set of leadsd is used on each surgical procedure. Additionally, since the lead assembly is intended to remain permanently attached to such an electrode, the connector may be designed to limit the likelihood of inadvertent detachment of the leads from the electrode. Further, such electrodes eliminate the need to sterilize leads after each surgical procedure.

A number of different, permanent lead connection arrangements have been utilized. Typically, a layer of foil or metallized plastic in an electrode is in electrical contact with a layer of electrically conductive gel held against the patient's skin or is coupled capacitively to the patient's skin by means of an overlying sheet of dielectric material. The lead ends may be attached to the foil sheet by means of crimp elements which engage the lead wire ends, the foil sheet, and perhaps other layers of foam material in the electrode. Alternatively, a metal stud, extending through the foil layer, may have a lead wire attached by a ring type terminal crimped therearound. As yet another alternative, the foil layer may define a tab against which lead terminals are secured by a covering layer of adhesive coated foam.

It is desirable to provide a connector for permanent attachment of conductor leads to a medical electrode in which the electrode is positively engaged, in which lead terminals on the ends of the lead wires are securely held in electrical contact with an electrically conductive layer of the electrode, and in which a strain relief for the leads is provided to reduce strain on the connector when a force is applied to the leads.

SUMMARY OF THE INVENTION

These needs are met by an electrical connector according to the present invention which provides electrical connection between a pair of electrical conductor leads, each having a ring terminals, and an electrically conductive connection tab of a medical electrode. The connector comprises an upper connector portion, a lower connector portion, and welded means for permanently attaching the upper and lower portions together. The upper connector portion defines a pair of engagement pins, spaced apart in correspondence to the spacing between the engagement holes defined by the tab. The lower connector portion defines a pair of engagement posts having outer diameters and spacing corresponding to the diameters and spacing of the pair of engagement holes, respectively. The posts each define a central opening sized to receive one of the engagement pins. The welded means extends around the periphery of the connector portions, whereby the engagement holes and the ring terminals are engaged by the engagement posts. The ring terminals and the connection tab are pressed together between the upper connector portion and the lower connector portion.

The engagement posts may each include at least one rib means on the periphery thereof to engage frictionally a terminal ring pressed thereon during assembly of the connector.

The welded means may comprise a ridge defined by the lower connector portion and extending around a portion of the periphery of the lower connector portion, and a corresponding surface extending around the periphery of the upper connector portion, to which said ridge is sonically welded, or permanently attached in some manner.

The upper and lower connector portions may define gaps in the sonic welded means which together define an access opening for the leads. The upper and lower connector portions may define outwardly curved surfaces to either side of the access opening, whereby tension applied to the conductor leads is transmitted to the outwardly curved surfaces, and thereby relieved from the ring terminals. The lower connector portion may further include separator means, centrally positioned adjacent the access opening, for urging the conductor leads outward into contact with the outwardly curved surfaces.

The upper connector portion may define at least one ring terminal contact element adjacent each of the engagement posts for pressing the ring terminals against the tab, thereby ensuring good electrical contact.

The upper connector portion may include a pair of locating recesses on either side of the access opening. The lower connector portion includes a pair of locating pins which mate with the locating recesses when the upper and lower connector portions are assembled.

Accordingly, it is an object of the present invention to provide an electrical connector having two portions which are permanently welded together to hold terminals on the ends of electrical conductor leads against an electrically conductive connection tab of a medical electrode; to provide such a connector in which at least one of the portions defines at least one post extending through an engagement hole in the connection tab; to provide such an electrical connector having a strain relief design; and to provide such an electrical connector which is easily assembled.

Other objects and advantages of the invention will be apparent from the following description, the accompanying drawings and the appended claims.

BRIEF DESCRIPTION OF THE DRAWINGS

FIG. 1 is an exploded view, showing the upper and lower connector portions, and portions of the medical electrode and the electrical conductor leads;

FIG. 3 is an enlarged plan view of the lower connector portion;

FIG. 4 is a sectional view taken generally along line 4—4 in FIG. 3;

FIG. 6 is a plan view of the upper connector portion; and

FIG. 7 is a sectional view, taken generally along line 7—7 in FIG. 6.

DETAILED DESCRIPTION OF THE PREFERRED EMBODIMENT

Figure 2:
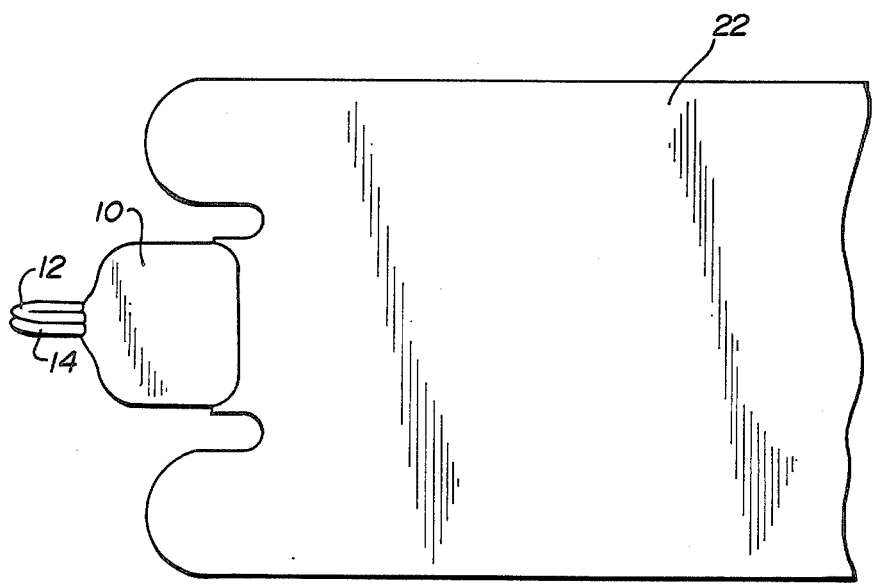
FIG. 2 is a plan view of the assembled connector and medical electrode.

Reference is made to FIGS. 1 and 2 which depict an electrical connector 10, constructed according to the present invention, for providing electrical connection between a pair of electrical conductor leads 12 and 14, each having a ring terminal 16 and 18 attached at the end thereof, and an electrically conductive tab 20 of a medical electrode 22, such as an electrosurgical patient electrode. Tab 20 defines a pair of engagement holes 24 and 26 and a slot 28 extending therebetween.

The electrode 22 may be of the electrically conductive type, which includes a layer of electrically conductive gel material, or the like (not shown), for contacting the skin of a patient, with a backing layer of electrically conductive material, such as a foil layer or a metallized plastic layer, which extends outward and is exposed on surface 30 of tab 20. Alternatively, the electrode 22 may be of the capacitively coupled type, in which the electrically conductive layer, extending onto surface 30 of tab 20, is electrically coupled to the skin of a patient through an overlying layer of dielectric material (not shown). In either event, the electrical connector of the present invention provides a means for electrically connecting the ring terminals 16 and 18 to the conductive surface 30 of tab 20 and maintaining the terminals in contact with conductive surface 30.

The electrical connector includes an upper connector portion 32, defining a pair of engagement pins 34, illustrated in FIGS. 6 and 7. The pins 34 are spaced apart in correspondence to the spacing between engagement holes 24 and 26.

The electrical connector further includes a lower connector portion 36 which defines a pair of engagement posts 38, shown in FIGS. 1 and 3. Posts 38 have outer diameters and spacing which correspond to the diameters and spacing of the pair of engagement holes 24 and 26. The posts each define a central opening 40 sized to receive a respective one of the engagement pins 34 when the upper and lower connector portions 32 and 36 are assembled together, with the terminals 16 and 18 and the tab 20 pressed between portions 32 and 36, as shown in FIG. 2. The portions 32 and 36 preferably are made of an electrically non-conductive, relatively ridge plastic material.

Figure 5:
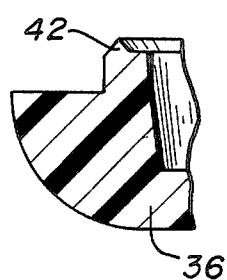
FIG. 5 is an enlarged partial sectional view taken generally along line 5—5 in FIG. 3.

The electrical connector further includes welded means, comprising a ridge 42 (FIGS. 3-5) and a corresponding surface 44 to which the ridge 42 may be sonically welded, or otherwise attached. As alternative attachment techniques, the ridge 42 and surface 44 may be permanently joined by an adhesive or a solvent or may be heated by a non-sonic method so as to fuse together. The welded means extends around the periphery of the connector portions 32 and 36 and holds the portions 32 and 36 together. When the connector is assembled, the engagement holes 24 and 26 and the ring terminals 16 and 18 are engaged by the engagement posts 38, and the ring terminals 16 and 18 and the connection tab 20 are pressed together between the upper connector portion 32 and the lower connector portion 36. The ridge 42 is defined by the lower connector portion 36 and extends around a portion of the periphery of the lower connector portion 36. Similarly, the surface 44 extends around a portion of the periphery of the upper connector portion 32. Additionally the top surfaces 45 of pins 34 may be sonically welded or otherwise attached to the bottoms of openings 40 in posts 38.

The engagement posts 38 may each include at least one rib means 46, and preferably several such rib means, extending longitudinally down the outer surfaces of the posts. Four such rib means are illustrated on each post 38 in FIG. 3, whereas three rib means are shown on each post 38 in FIG. 1. The connector portion 36 is typically injection molded from a relatively rigid plastic material. When the connector is to be assembled, the posts 38 are inserted through engagement holes 24 and 26. Next, the ring terminals 16 and 18 are placed over the posts 38. Because the inner diameter of the ring terminals 16 and 18 approximates the outer diameter of posts 38, the ribs 46 are distorted in shape as the rings 16 and 18 are forced onto the posts 38, producing an interference fit between the ring terminals 16 and 18 and the ribs 46. This holds the terminals 16 and 18 in position during the assembly operation, as the upper connector portion 32 is placed in position above the tab 28 and portions 32 and 36 are sonically welded together, or otherwise attached.

The upper and lower connector portions 32 and 36 define gaps 48 and 50 in the sonic welding means which, together, define an access opening for the leads 12 and 14 when the connector 10 is assembled. The upper and lower connector portions 32 and 36 also define outwardly curved surfaces 52 and 54 to either side of the access opening. Any force applied to the conductor leads 12 and 14 is transmitted to the outwardly curved surfaces 52 and 54, thereby reducing the level of the force applied to the ring terminals 16 and 18. This reduces the likelihood of the ring terminals 16 and 18 becoming separated from the leads 12 and 14. The lower connector portion 36 further comprises separator means 56 which is centrally positioned adjacent the access opening, for urging the conductor leads outward into contact with the outwardly curved surfaces 52 and 54.

The upper connector portion defines ring terminal contact elements 58 which are positioned adjacent each of the engagement posts 34 and which press the ring terminals 16 and 18 against the tab surface 30. This further insures good electrical contact when the connector 10 is assembled. Assisting in proper alignment of the upper connector portion 32 and the lower connector portion 36 during assembly are a pair of locating pins 60 on the lower connector portion 36. Pins 60 mate with locating recesses 62 in the upper connector portion 32.

It will be appreciated that the electrical connector of the present invention provides a simple, reliable means of securely attaching a lead assembly to a connection tab of a medical electrode and for maintaining good electrical contact. The connector is simply assembled and the upper and lower portions are secured together by a sonic welding operation which may be accomplished economically and rapidly.

Having described the invention in detail and by reference to preferred embodiments thereof, it will be apparent that modifications and variations are possible without departing from the scope of the invention defined in the appended claims.

What is claimed is:

1. An electrical connector for providing electrical connection between each of a pair of electrical conductor leads, each having a ring terminal, and an electrically conductive connection tab of a medical electrode, said tab defining a pair of engagement holes, comprising:
   an upper connector portion defining a pair of engagement pins spaced apart in correspondence to the spacing between said engagement holes,
   a lower connector portion defining a pair of engagement posts having outer diameters and spacing corresponding to the diameters and spacing of said pair of engagement holes, respectively, said posts each defining a central opening sized to receive one of said engagement pins, and
   welded means, positioned around the periphery of said connector portions, for permanently attaching said portions together, with said engagement holes and said ring terminals engaged by said engagement posts, whereby said ring terminals and connection tab are pressed together between said upper connector portion and said lower connector portion.

2. The electrical connector of claim 1 in which said engagement posts each include at least one rib means on the periphery thereof to engage frictionally a ring pressed thereon during assembly of said connector.

3. The electrical connector of claim 1 in which said welded means comprises a ridge defined by said lower connector portion and extending around a portion of the periphery of said lower connector portion, and a corresponding surface, extending around a portion of the periphery of said upper connector portion, to which said ridge is bonded.

4. The electrical connector of claim 3 in which said ridge and said corresponding surface are sonically welded together.

5. The electrical connector of claim 4 in which said lower connector portion further comprises separator means, centrally positioned between said engagement posts and adjacent said access opening, for urging said conductor leads outward into contact with said outwardly curved surfaces.

6. The electrical connector of claim 1 in which said upper and lower connector portions define gaps in said welded means which together define an access opening for receiving said leads.

7. The electrical connector of claim 5 in which said upper and lower connector portions define outwardly curved surfaces to either side of said access opening and contiguous with said conductor leads, whereby tension applied to said conductor leads is transmitted to said outwardly curved surfaces, thereby reducing the force applied to said ring terminals.

8. The electrical connector of claim 6 in which said upper connector portion includes a pair of locating recesses on either side of said access opening adjacent said welded means, and said lower connector portion includes a pair of locating pins which mate with said locating recesses when said upper and lower connector portions are assembled.

9. The electrical connector of claim 1 in which said upper connector portion defines at least one ring terminal contact element adjacent each of said engagement posts for pressing said ring terminals against said tab, thereby insuring good electrical contact.

10. The electrical connector for providing electrical connection between a lead wire assembly, including at least one lead wires having a terminal at the end thereof, and a connection tab of a medical electrode having at least one engagement hole, comprising:
    an upper connector portion, defining at least one engagement pin,
    a lower connector portion, defining at least one engagement post, having an outer diameter corresponding to the diameter of said engagement hole, said post defining a central opening sized to receive said engagement pin, and
    welding means, extending around at least a portion of the periphery of said upper and lower connector portions for securing said portions together, with said engagement post extending through said engagement hole and said terminal is pressed against terminal, whereby said connection tab.

11. The electrical connector of claim 10 in which said welding means comprises a ridge extending around a portion of the periphery of said lower connector portion and a corresponding surface on said upper connector portion to which said ridge is permanently secured.

12. The electrical connector of claim 11 in which said ridge and said corresponding surface are fused together.

13. The electrical connector of claim 10 in which said upper and lower connector portions define an access opening for said lead wires.

14. The electrical connector of claim 12 in which said upper and lower connector portions define an access opening for said lead wires and outwardly curved surfaces on opposite sides of said access opening, and in which said connector further includes separator means, centrally positioned adjacent said access opening for urging said lead wires outward into contact with said outwardly curved surfaces, such that tension applied to said lead wires is transmitted to said curved surfaces.

* * * * *

UNITED STATES PATENT AND TRADEMARK OFFICE
CERTIFICATE OF CORRECTION

PATENT NO. : 4,738,263

DATED : April 19, 1988

INVENTOR(S) : Timothy B. Seebach, James R. Crawford

It is certified that error appears in the above-identified patent and that said Letters Patent is hereby corrected as shown below:

```
Col. 2, line 1 "leadsd" should be --leads--.
Col. 6, line 3, after "ring" insert --terminal--.
```

Signed and Sealed this

Twenty-third Day of August, 1988

Attest:

DONALD J. QUIGG

*Attesting Officer*  *Commissioner of Patents and Trademarks*